US 11,266,789 B2

(12) United States Patent
Lefebvre et al.

(10) Patent No.: US 11,266,789 B2
(45) Date of Patent: Mar. 8, 2022

(54) MULTI-DOSE DISPENSER

(71) Applicant: VIRBAC, Carros (FR)

(72) Inventors: Christelle Lefebvre, Saint Laurent du Var (FR); Michel Robin, Antibes (FR)

(73) Assignee: VIRBAC, Carros (FR)

( * ) Notice: Subject to any disclaimer, the term of this patent is extended or adjusted under 35 U.S.C. 154(b) by 435 days.

(21) Appl. No.: 16/468,447

(22) PCT Filed: Dec. 11, 2017

(86) PCT No.: PCT/EP2017/082229
§ 371 (c)(1),
(2) Date: Jun. 11, 2019

(87) PCT Pub. No.: WO2018/108817
PCT Pub. Date: Jun. 21, 2018

(65) Prior Publication Data
US 2021/0283334 A1  Sep. 16, 2021

(30) Foreign Application Priority Data
Dec. 12, 2016 (FR) ...................................... 1662305

(51) Int. Cl.
*A61M 5/315* (2006.01)
*A61M 5/31* (2006.01)
(52) U.S. Cl.
CPC ...... *A61M 5/3158* (2013.01); *A61M 5/31505* (2013.01); *A61M 5/31578* (2013.01);
(Continued)
(58) Field of Classification Search
CPC ............ A61M 5/3158; A61M 5/31595; A61M 2005/31508; A61M 5/31576;
(Continued)

(56) References Cited

U.S. PATENT DOCUMENTS

| 4,261,359 A | 4/1981 | Chein |
| 5,147,323 A * | 9/1992 | Haber .................... A61M 5/19 604/191 |

(Continued)

FOREIGN PATENT DOCUMENTS

| WO | 93/11813 A1 | 6/1993 |
| WO | 94/07562 A1 | 4/1994 |

OTHER PUBLICATIONS

International Search Report and Written Opinion dated Apr. 9, 2018 issued in corresponding application No. PCT/EP2017/082229; w/ English partial translation and partial machine translation (25 pages).

*Primary Examiner* — Bhisma Mehta
*Assistant Examiner* — Phoebe Anne Staton
(74) *Attorney, Agent, or Firm* — Seckel IP, PLLC (57) ABSTRACT

Multi-dose dispenser comprising: a product reservoir (14), on the X-axis, opening at a distal end through an outlet orifice and comprising a barrel (24); a piston (20) comprising a piston rod (38) having a rack and, at a distal end of the piston rod, a piston head (34) slidably mounted in the barrel (24) along the X-axis; a pawl mounted so as to be movable along the X-axis relative to the reservoir and configured to cooperate with the rack so as to drive the piston along the X-axis only in a forward direction of the piston in the barrel; a spring arranged to push the pawl back along the X-axis in a reverse direction; a case containing the pawl and at least a part of the piston; and a check valve arranged to seal the outlet orifice and allow only an outlet of product from the reservoir.

25 Claims, 6 Drawing Sheets

(52) U.S. Cl.
CPC . *A61M 5/31593* (2013.01); *A61M 2005/3104* (2013.01); *A61M 2005/3126* (2013.01); *A61M 2005/3128* (2013.01); *A61M 2005/31508* (2013.01); *A61M 2207/00* (2013.01)

(58) Field of Classification Search
CPC .. A61M 2005/3104; A61M 2005/3126; A61M 5/31578; A61M 5/31505; A61M 5/31593; A61M 5/31585; A61M 5/31526; A61M 5/31551; A61M 2005/3128; A61M 35/00; A61M 35/003; A61M 5/504; A61M 5/50; A61M 5/3202; A61M 2005/208; A61M 2005/2073; A61M 5/3134; A61M 5/3129; A61M 5/31568; A61M 5/3286; A61B 5/15117; A61B 17/00491; A61D 7/00; A61D 1/025; B05C 17/012; B05C 17/005; B01F 13/0025; A47K 5/122
See application file for complete search history.

(56) References Cited

U.S. PATENT DOCUMENTS

| | | | |
|---|---|---|---|
| 5,624,402 A * | 4/1997 | Imbert | A61M 5/3134 604/111 |
| 5,772,665 A * | 6/1998 | Glad | A61M 5/284 604/82 |
| 6,102,896 A * | 8/2000 | Roser | A61M 5/28 604/124 |
| 8,540,124 B2 | 9/2013 | Francavilla | |
| 9,033,936 B2 * | 5/2015 | Holmqvist | A61M 5/31555 604/208 |
| 2008/0070187 A1 * | 3/2008 | Mulhauser | A61C 5/62 433/89 |
| 2011/0129288 A1 * | 6/2011 | Uehara | B05C 17/0133 401/152 |
| 2012/0184917 A1 | 7/2012 | Bom et al. | |

* cited by examiner

MULTI-DOSE DISPENSER

TECHNICAL FIELD

The invention concerns a multi-dose dispenser for the application of a liquid product, in particular a veterinary product, to the surface of an animal's skin.

PRIOR ART

To apply a liquid product on the skin of an animal, it is known to use single-dose pipettes, called "spot-ons". A pipette cannula is placed on the animal's skin and the product reservoir is compressed to eject the product from the pipette.

A single-dose pipette has the advantage of perfect hygiene, since it is only used once. However, it does produce significant quantities of packaging.

Moreover, when a treatment requires several successive applications, the use of single-dose pipettes does not make it easy to determine the number of applications already administered. Finally, a single-dose pipette only allows the administration of a same volume of product. It is in effect not possible to split the administration of the product contained in the reservoir.

U.S. Pat. No. 8,540,124 discloses an example of a multi-dose dispenser that partially addresses the drawbacks of single-dose pipettes.

However, there is still an ongoing need for a multi-dose dispenser that is:
- ergonomic, in particular for the application of compounds to potentially nervous animals:
- compact, to facilitate storage and packaging;
- of limited manufacturing cost;
- guaranteeing perfect conditions of hygiene;
- limiting the risk of improper handling, especially to protect children;
- easy to recycle;
- clean, reliable and easy to use.

One object of the present invention is to satisfy, at least partially, this need.

SUMMARY OF THE INVENTION

The invention proposes a multi-dose dispenser comprising:
- a product reservoir, on the X-axis, opening at a distal end through an outlet orifice and comprising a barrel;
- a piston comprising
  - a piston rod having a rack and,
  - at a distal end of the piston rod, a piston head slidably mounted in the barrel along the X-axis;
- a pawl mounted so as to be movable along the X-axis relative to the reservoir and configured to cooperate with said rack so as to drive the piston along the X-axis only in a forward direction of the piston in the barrel;
- preferably, a case preferably containing the pawl and preferably at least part of the piston, and preferably at least part of the reservoir, and in particular the barrel of the reservoir;
- preferably a cap adapted to selectively seal, in a closed position, an orifice for ejecting the product from the dispenser.

According to a first main aspect of the invention, the dispenser has a spring arranged to push the pawl back along the X-axis in a direction opposite to the forward direction, the spring forming a one-piece part with the pawl, preferably being made in one piece with the pawl.

This reduces the number of parts in the dispenser, making assembly easier and reducing manufacturing costs.

In particular, for the first main aspect of the invention, a dispenser according to the invention may further comprise one or more of the following optional and preferred features:
- the spring is a leaf spring;
- the spring has at least one spring arm diverging from the X-axis, following the forward direction, i.e. moving increasingly away from the X-axis as one follows the X-axis;
- said spring arm extends in a plane including the X-axis;
- the spring arm tapers away from the X-axis, following the forward direction, preferably maintaining a constant width, the width being measured perpendicular to the plane in which said spring arm extends;
- the spring arm, preferably each spring arm, is arranged between two guide ribs, preferably substantially parallel, preferably parallel to the X-axis, configured to guide the deformation of the spring arm in a plane parallel to the X-axis, preferably in a plane passing through the X-axis;
- the guide ribs are made in one piece with the case;
- the spring arm has an abutment end immobilized in relation to the barrel, preferably by abutting against a shoulder of the case;
- the spring comprises said first and second spring arms, preferably coplanar, preferably identical, each spring arm diverging preferably from the X-axis, following the forward direction, from a common base and extending, preferably, in the same plane including the X-axis;
- the base is made in one piece with said first and said second spring arms, the assembly being preferably made of a polymeric material, preferably plastic;
- the first and second spring arms are substantially identical and extend symmetrically relative to the X-axis. Advantageously, the action of the spring arms does not destabilize the piston movement.

According to a second main aspect of the invention, the rack has first and second rows of teeth, said rows of teeth extending parallel to the X-axis, and the pawl has first and second clamp portions arranged to elastically clamp said rack by pressing on said first and second rows of teeth, respectively.

Such a configuration allows for quick assembly. In addition, the forces exerted by the clamp portions on the rows of teeth may be balanced, which stabilizes the piston during its displacement along the X-axis.

Notably, for the second main aspect of the invention, a dispenser according to the invention may further have one or more of the following optional and preferred features:
- the first and second rows of teeth extend in straight lines, preferably substantially parallel, preferably in a plane including the X-axis;
- the first and second rows of teeth are arranged on opposite sides of said piston rod, and preferably made in one piece with said piston rod;
- the first and second rows of teeth are the same length;
- the first and second rows of teeth extend over more than 60%, more than 80%, more than 90%, preferably substantially 100% of the length of the piston rod;
- the pawl has first and second pawl arms, preferably extending parallel to the X-axis, ending with said first and second clamp portions, respectively, the piston rod extending, for more than 60%, more than 80%, more than 90%, more than 95%, preferably substantially 100% of its length, between said first and second pawl arms, preferably at least in the initial configuration of the dispenser;

the length of the first and second pawl arms is substantially equal to the length of the piston rod;

the pawl comprises at least one, preferably first and second stop arms, preferably each extending in a plane perpendicular to the X-axis, preferably coplanar, each stop arm being preferably attached on a respective pawl arm, and preferably made in one piece with said respective pawl arm, each stop arm being configured to limit the displacement of the pawl, along the X-axis, in the forward direction;

the pawl, the spring and the stop arms form a one-piece part, preferably made of a polymeric material, preferably plastic;

the pawl arm, preferably each pawl arm, is arranged between two guide ribs, preferably substantially parallel, preferably parallel to the X-axis, configured to guide the displacement of said pawl arm in a plane parallel to the X-axis, preferably in a plane passing through the X-axis;

said guide ribs are configured to guide the displacement of one or more stop arms in a plane passing through the X-axis;

the guide ribs are made in one piece with the case;

According to a third main aspect of the invention, the dispenser comprises at least one, preferably two, preferably three, preferably four piston displacement guide ribs, each guide rib comprising two large sides, preferably substantially parallel to each other, connected to each other by an edge, each guide rib being configured to provide a sliding contact for said edge and/or one of said large sides on the piston, preferably on the piston rod.

As will appear in greater detail later in the description, such guide ribs provide a high degree of compactness and limit the material consumption and the weight of the dispenser. Moreover, they facilitate the positioning of the various parts, and in particular the piston, when assembling the dispenser.

In particular for the third main aspect of the invention, a dispenser according to the invention may further comprise one or more of the following optional and preferred features:

said at least one guide rib is shaped to provide a sliding contact both by its edge and by one of its large sides;

the dispenser has two pairs of so-called guide ribs, the guide ribs being preferably substantially flat, more preferably parallel to each other;

each guide rib of one said pair of guide ribs is coplanar to a guide rib of the other pair of guide ribs;

the two guide ribs of a pair of guide ribs, preferably each pair of guide ribs, are parallel to the X-axis;

the two guide ribs of a pair of guide ribs, preferably each pair of guide ribs, have substantially the same height;

the height of a guide rib, preferably of each guide rib, is greater than 5 mm, preferably greater than 10 mm and/or less than 30 mm;

the edge of a guide rib, preferably of each guide rib, extends straight, parallel to the X-axis;

each guide rib is flat and extends parallel to a second guide rib and in the plane of a third guide rib;

the spacing of two guide ribs of a pair of guide ribs is substantially equal to the width of one, preferably of each pawl arm, and/or of one, preferably of each spring arm, and/or of one, preferably of each stop arm, the width being measured perpendicular to a plane wherein said pawl arm(s) and/or said spring arm(s) and/or said stop arm(s) extend;

the spacing of the two guide ribs of at least one pair of guide ribs, preferably each pair of guide ribs, is substantially equal to the width of a respective pawl arm and/or of a spring arm and/or of a stop arm, so as to guide the deformation and/or displacement, in a plane parallel to the X-axis, of said pawl arm and/or said spring arm and/or said stop arm, respectively;

preferably each pawl arm, and preferably each spring arm, and preferably each stop arm is guided between the guide ribs of one of said pairs of guide ribs;

at least one, preferably each, guide rib is configured to guide the sliding, along the X-axis, of a corresponding corner located on the piston rod;

the side of one said corner, preferably any corner, in sliding contact with a large side of the respective guide rib, is delimited by a straight edge, preferably parallel to the X-axis, the length of which along the X-axis is preferably greater than 20%, 30%, 50%, 60%, 80%, 90%, preferably substantially 100% of the length of the piston rod;

at least one, preferably at least two, preferably at least three, preferably four said corners extend along a row of teeth of the rack;

at least one, preferably each, guide rib is made in one piece with the case.

According to a fourth main aspect of the invention, the dispenser has a deactivatable, preferably irreversibly, preferably breakable, locking device, configured to prevent the administration of a product contained in the reservoir, and arranged inside the case.

The arrangement of the locking device inside the case advantageously limits the risk of injury during its deactivation, particularly when it is deactivated as a result of a sudden break. It also limits the risk of unintentional damage to the locking device.

In particular for the fourth main aspect of the invention, a dispenser according to the invention may further have one or more of the following optional and preferred features:

the locking device is arranged in such a way that before its deactivation, it immobilizes the piston (locking it in position);

before deactivation, the locking device is attached on the piston, preferably on the piston rod, and after deactivation, it is free relative to the piston, preferably the piston rod, respectively;

the locking device is connected to the piston, preferably to the piston rod, by a weakened zone, preferably in the form of a weakened line, preferably extending perpendicular to the X-axis, the weakened zone resulting preferably from a local reduction of at least one dimension of the cross-section of the locking device in a plane parallel to the X-axis, preferably from a reduction of the thickness or from the arrangement of holes through the locking device;

the locking device is connected to the distal end of the piston rod, i.e. the end of the piston rod on the side of the outlet orifice;

before deactivating the locking device, the piston rod and the locking device constitute a one-piece part;

the locking device is made in one piece with the piston rod, and is preferably manufactured by injecting a polymeric material, preferably plastic, into a mold;

the locking device is deactivatable by pressing on a deactivation device, arranged, at least in part, outside the case, preferably by simply pressing it with one's thumb;

the locking device is deactivatable by an action suitable to administer a dose of product, preferably by pressing a push-button along the X-axis;

the push-button is mechanically coupled to said pawl, i.e. the displacement of the push-button, in particular to administer a dose, causes the displacement of the pawl;

the locking device may be deactivated by a force, preferably exerted on the pawl, preferably by means of a push-button, of less than 10 N, 5 N, 3 N, 1 N. In one embodiment, the deactivation of the locking device may thus be hardly perceptible by the operator;

alternatively, the force may be greater than 3 N, greater than 5 N or even greater than 10 N, which is particularly useful when the locking device is used to confirm to the operator that the dispenser has never been used;

the deactivation device is a push-button, preferably mechanically coupled to the pawl, preferably movable along the X-axis, the locking device obstructing said movability before the deactivation thereof;

the locking device is in the shape of a tab, preferably in the shape of two tabs;

the locking device extends substantially in a plane perpendicular to the X-axis;

the locking device has two tabs, preferably only two tabs, preferably substantially aligned, more preferably aligned along an axis intersecting the X-axis;

the locking device is attached, preferably by clipping, to the case;

the locking device extends at least partially between two guide ribs of the piston, preferably of the piston rod, preferably in contact with said guide ribs, which thus contribute to keeping the locking device in position;

the locking device has a stop pin configured to limit the displacement of the pawl along the X-axis, in the forward direction, preferably in such a way that the stroke of said pawl is equal to the length of one or more teeth of the rack, preferably equal to the length of one tooth.

According to a fifth main aspect of the invention, a dispenser according to the invention has a check valve, arranged to seal the outlet port and allow only an outlet of product from the reservoir.

The check valve may thus open when the piston advances in the barrel and close as soon as this advancement stops. Advantageously, the check valve isolates the product contained in the barrel from the outside, which stabilizes the physical-chemical conditions inside the barrel, and limits in particular the oxidation of the product. The check valve also limits any evaporation of the product.

The check valve hinders, preferably prevents, an inlet of air, and thus advantageously prevents any reverse movement of the piston.

Finally, the check valve limits the free flow out of the applicator tip, allowing the doses administered to be controlled with precision.

Notably, for the fifth main aspect of the invention, a dispenser according to the invention may further comprise one or more of the following optional and preferred features:

the check valve has a flange, preferably annular, sandwiched between the reservoir, preferably a distal end of the reservoir, preferably a distal end of a cannula of the reservoir opening into the barrel, and an applicator tip rigidly integral with the reservoir, preferably so that the flange establishes a seal between said distal end and the applicator tip; the check valve may thus be used to prevent any passage of product between the applicator tip and the reservoir, and in particular between the applicator tip and the cannula of the reservoir on which the applicator tip is mounted;

a duct, preferably defined by the applicator tip, extends from said check valve to the ejection orifice through which product initially contained in the reservoir may be ejected from the dispenser;

the check valve is a drop recovery valve, i.e. the closure of which creates a suction that returns the product contained in said duct, i.e. downstream of the check valve, to the side of the check valve opposite said duct, i.e. upstream of the check valve;

the cap has a stud arranged to penetrate into said duct in the closed position of the cap, preferably to close, preferably in a sealed manner, said duct;

the stud is configured to abut against the check valve, preferably in a sealed manner, in the closed position of the cap.

According to a sixth main aspect of the invention, a dispenser according to the invention has an indicator label attached, by a proximal end, on the piston and has a free distal end arranged against the outer surface of the barrel.

Advantageously, the displacement of the piston, along the X-axis, in the forward direction, drives that of said distal end of the indicator label along the X-axis in the reverse direction opposite to the forward direction. The displacement of the indicator label is in proportion to the piston's advancement, and thus to the number of doses administered. The indicator label thus constitutes a simple and reliable means of indicating, for example, the number of doses already administered or still to be administered.

Notably, for the sixth main aspect of the invention, a dispenser according to the invention may further have one or more of the following optional features:

the dispenser comprises a case wherein is housed the barrel of the reservoir and wherein the distal end of the indicator label is arranged between the barrel and the case;

the case, preferably opaque, provides a window through which a portion of the indicator label is visible from the outside of the case;

the indicator label has indicators, the pitch between two successive indicators along the X-axis being constant and preferably equal to the dosing stroke, i.e. the maximum distance that the pawl may travel along the X-axis in the forward direction;

the window is sized in such a way that one or two indicators, preferably only one indicator, is visible;

the indicators are numbers that increase or decrease along the X-axis, the progression between two adjacent numbers being one unit;

the indicators are arranged so that the number appearing in the window is equal to the number of doses already administered or to the number of doses remaining to be administered;

the distal end of the indicator label is attached to a distal end of the piston rod;

the indicator label rests on a straight portion of a flange of a proximal opening of the barrel, an opening through which the piston head is introduced into the barrel;

the straight portion extends in a plane perpendicular to the X-axis;

the indicator label rests on the edge of at least one, preferably several, support ribs projecting from the outer surface of the barrel and extending preferably in a plane parallel to the X-axis;

the edge of said preferably substantially straight support rib extends from said straight portion of the flange of the barrel and preferably to the outer surface of the barrel;

the length of the support ribs is preferably greater than 0.3 times, preferably greater than 0.4 times the length of the part of the indicator label which, in the initial configuration of the dispenser, i.e. before the administration of the first dose, extends along the barrel, on the outside of the barrel.

In general, the invention may comprise one or more of the following optional features:

the barrel contains a liquid or paste product, preferably a veterinary product, more preferably a pest control product;

the dispenser comprises an applicator tip with an atraumatic distal end, preferably substantially ovoid, or even spherical, or with beveled edges, intended to come into contact with the skin of an animal to be treated;

the dispenser comprises a removable applicator tip;

the cap is designed in such a way that the dispenser is stable, i.e. it does not tip when resting "head down", i.e. exclusively resting on the cap in the closed position, on a flat surface inclined by 10°, preferably 15°, preferably 20° with a horizontal plane, regardless of the piston position;

the cap has a front surface dimensioned so that the vertical axis passes through the barycenter of the dispenser through said front surface when the dispenser is placed upside down on an inclined plane of 5°, preferably 10°, preferably 15°, preferably 20°, relative to a horizontal plane;

the pawl is housed in the case and the dispenser comprises a push-button projecting out of the case and muffled so as to be movable along the X-axis relative to the case, the push-button being mechanically coupled with the pawl so that pressing said push-button in the forward direction advances the pawl in the forward direction;

the dispenser comprises only:
  the case,
  the reservoir,
  the piston,
  preferably an indicator label,
  a slider, preferably in one piece, consisting of the pawl and the spring, and preferably the stop arms,
  preferably an applicator tip and
  preferably a push-button.

Obviously, the features described above, and in particular the features of a dispenser according to any of the main aspects of the invention, may be combined.

The invention further concerns a method for the manufacture of a dispenser according to the fourth main aspect of the invention, this method comprising the following successive steps:

a) assembly of the various components of said dispenser and filling of the barrel with a liquid product, preferably a veterinary product;

b) deactivation of the locking device;

c) packaging of said dispenser in a package, preferably a hermetic package.

Advantageously, a manufacturing method according to the invention makes it possible to obtain a ready-to-use packaged dispenser, without the need to deactivate the locking device.

Preferably, in step b), the piston is advanced into the barrel so as to fill, at least partially, preferably completely, the applicator tip with said liquid product. The dispenser is thus "primed", so that once the buyer has removed the dispenser from its packaging, he may immediately use it to administer a precise dose.

Preferably, the priming and deactivation of the locking device is achieved by pressing the same push-button mechanically coupled to the pawl of the dispenser.

Finally, the invention concerns a dispenser manufactured following a method according to the invention. In particular, the invention concerns a dispenser according to the invention packaged in a package, preferably hermetic, and preferably comprising a locking device that has been deactivated.

Definitions

"Liquid" means a product that is not solid or gaseous. This term thus includes paste products.

A "longitudinal" plane is a plane parallel to the X-axis.

A "radial" plane is a plane that includes the X-axis.

A "transverse" plane is a plane perpendicular to the X-axis.

To describe in detail, for the sake of clarity, a plane parallel to the plane wherein the slider extends is called the "horizontal plane". The "median" horizontal plane is the horizontal plane containing the X-axis.

A "vertical plane" is a plane perpendicular to a horizontal plane. A vertical "longitudinal" plane is a vertical plane parallel to the X-axis. The "median" vertical longitudinal plane is the vertical longitudinal plane which includes the X-axis.

"Distal" and "proximal" are used to describe relative positions of parts or portions of parts along the X-axis, a "distal" part or portion of a part being closer to the end of the dispenser on the side of the product applicator tip than a "proximal" part or portion of a part.

As the product flows to the distal end of the dispenser, "distal" and "proximal" positions may also be qualified as "downstream" and "upstream", respectively.

A "rib" is a thin, blade-shaped projection, preferably 2, 3, 5 or 10 times less than the length. Preferably, the height of a rib is greater than its thickness, or even greater than 2, 3, 5, even 10 times its thickness.

Unless otherwise specified, the verbs "include", "comprise" or "have" should be interpreted broadly, i.e. in a non-exclusive manner.

BRIEF DESCRIPTIONS OF THE FIGURES

Other features and advantages of the invention will further appear when reading the detailed description that follows, and when examining the accompanying drawing wherein:

FIG. 3 shows, in perspective, different parts of the dispenser of FIGS. 1 and 2, FIGS. 3a and 3b showing the half-cases, FIG. 3c showing the slider, FIGS. 3d and 3e showing the one-piece assembly comprising the piston rod and the tabs, FIGS. 3f and 3g showing the applicator tip, FIG. 3h showing the reservoir and FIGS. 3i and 3j showing the two components of the cap, before assembly;

FIG. 4 is a cross-sectional view of details of the dispenser in FIGS. 1 and 2, with FIGS. 4a, 4b and 4c illustrating the guidance of the piston rod, the check valve and the teeth, respectively.

Identical references are used to designate similar or identical devices. An index makes it possible to distinguish these devices. However, the reference without an index is used to designate, in a generic way, a set of similar or identical devices.

The median vertical longitudinal plane separates the space into two half-spaces. References may be marked with a sign "a" or "b" depending on whether they refer to parts or portions of parts that extend into the first or second half-space, respectively.

DETAILED DESCRIPTION

General Structure

The figures represent a preferred embodiment of a dispenser 10 according to the invention. This dispenser comprises a case 12, a reservoir 14, an applicator tip 16, a removable cap 18, a piston 20 having a rack, and a button 22 comprising a pawl cooperating with the rack to advance, irreversibly and by the action of an operator, the piston 20 in the reservoir 14, so as to push the product contained in the reservoir towards the applicator tip 16.

The case 12 has two half-cases 12a and 12b attached to each other, for example by clipping, gluing or welding. These two half-cases define a substantially tubular inner volume, on the X-axis, wherein the reservoir 14 and the piston 20 are housed.

The case 12 has lugs 13a and 13b, preferably arranged near the proximal end of the case 12, and preferably made in one piece with the half cases 12a and 12b, respectively. The lugs 13a and 13b are shaped to serve as an abutment surface for the index and middle fingers of the operator's hand, respectively, to hold the case 12 when the operator presses the button 22 with his thumb.

Figure 3A:
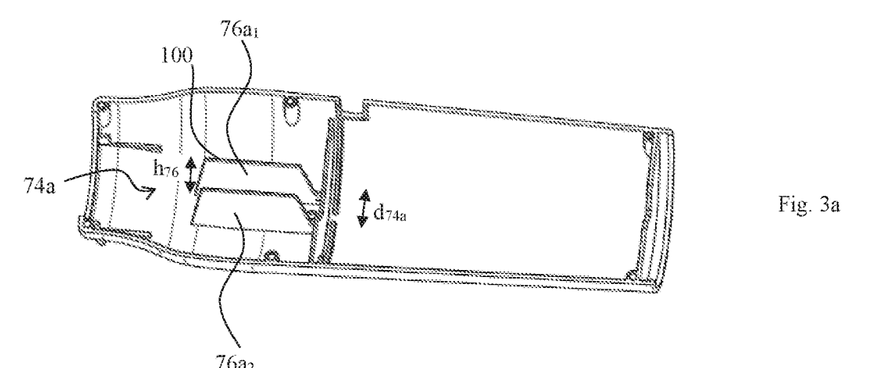
Figure 3B:
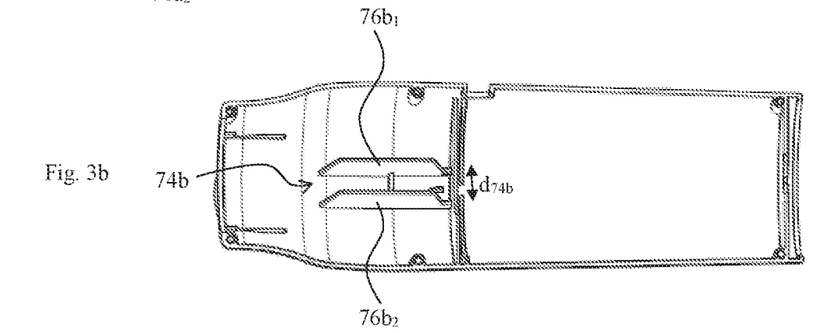
Figure 3C:
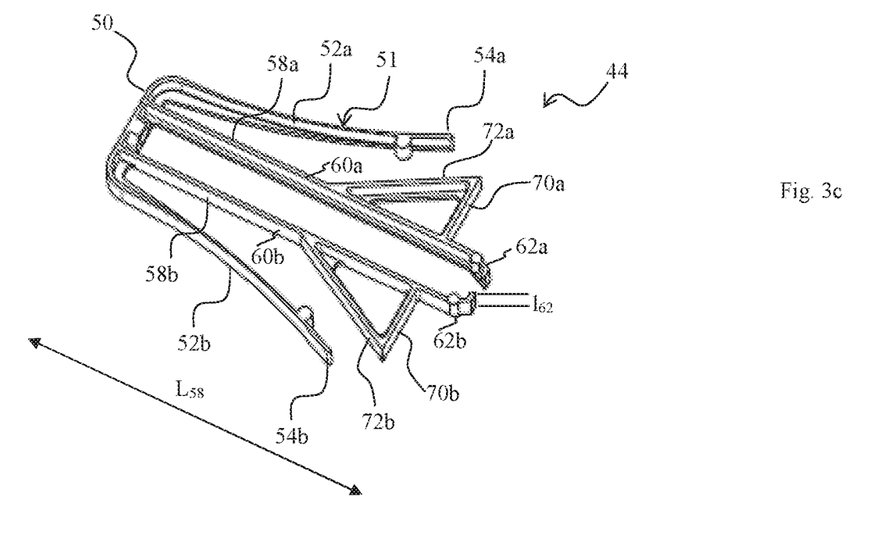

The reservoir 14 has a barrel 24 and a cannula 26. The barrel 24, on the X-axis, has a constant cross-section, preferably circular. The lumen 28 of the cannula 26 opens into the bottom of the barrel 24 and, at the opposite distal end 29, through an outlet orifice 32 (FIG. 3h).

Figure 1:
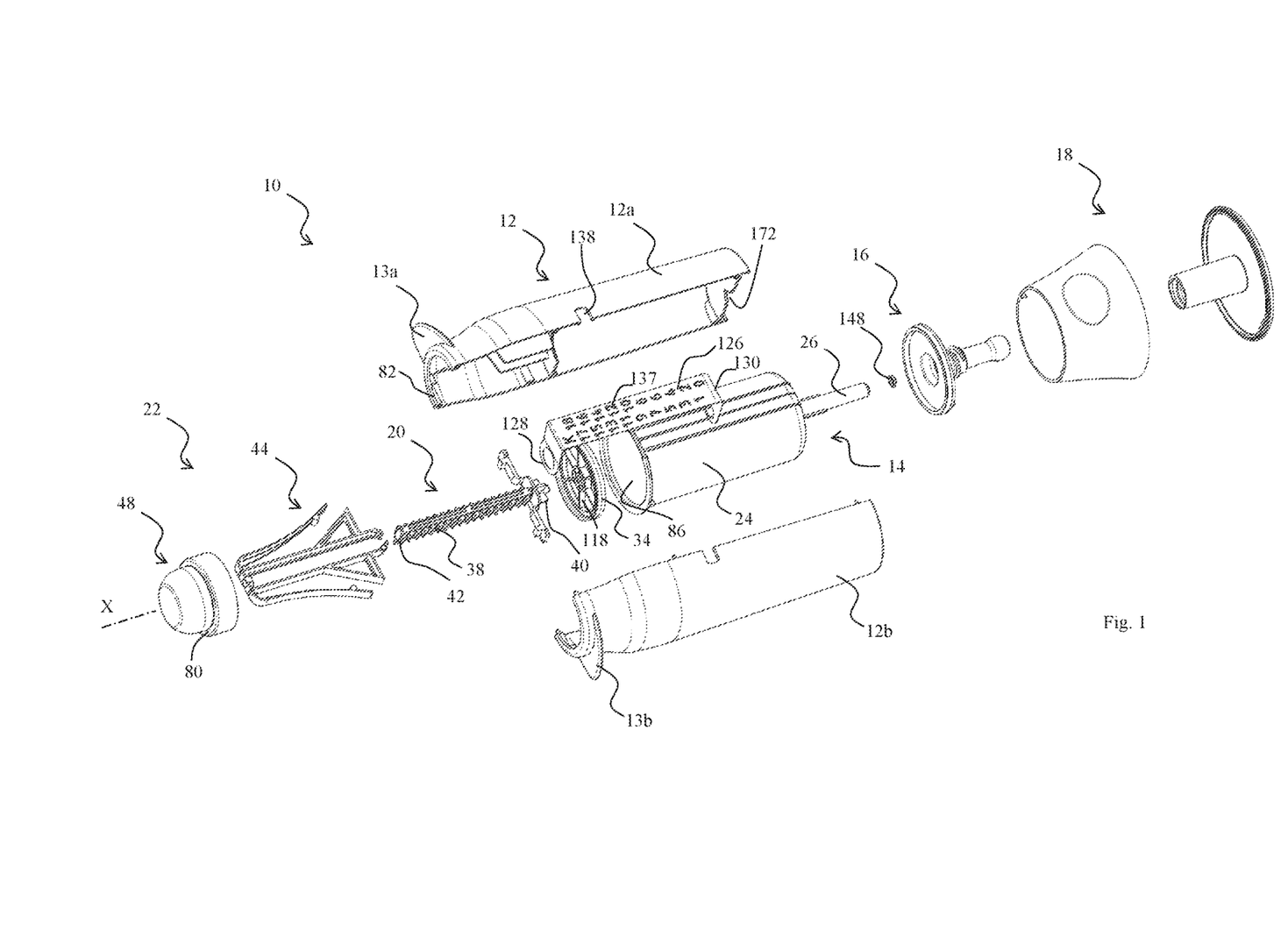
FIG. 1 shows, in exploded view, a dispenser according to a preferred embodiment of the invention.
Figure 2A:
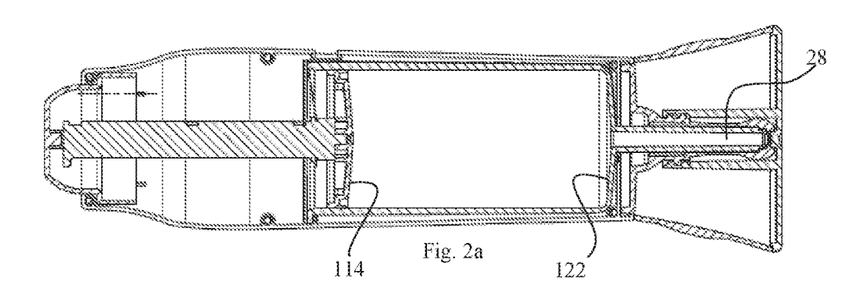
Figure 2B:
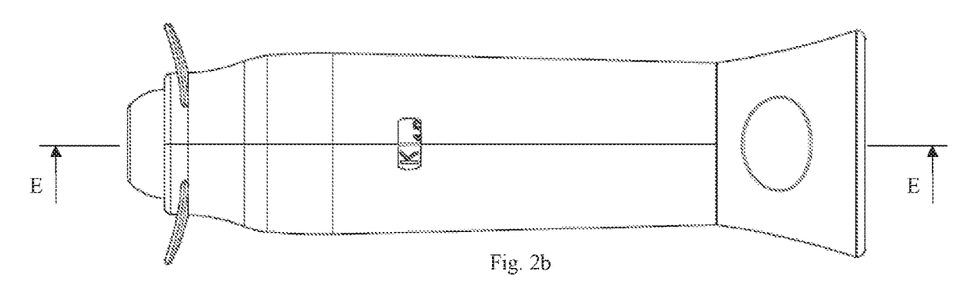
FIG. 2 (FIGS. 2a-2h) shows the dispenser of FIG. 1 after assembly, FIGS. 2a, 2d and 2h showing the dispenser according to the median vertical sections E-E, median horizontal sections B-B and cross sections F-F, respectively.
Figure 2C:
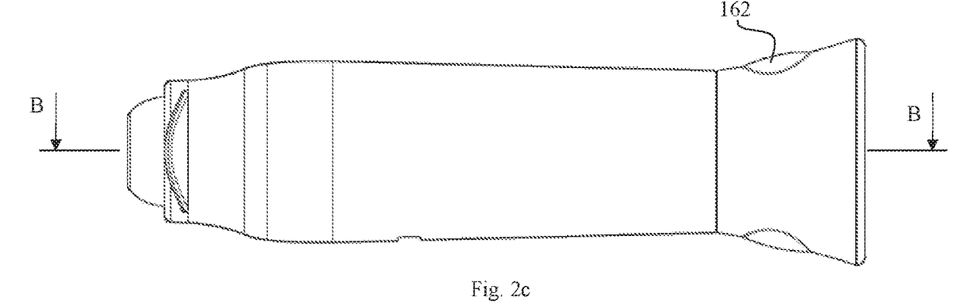
Figure 2D:
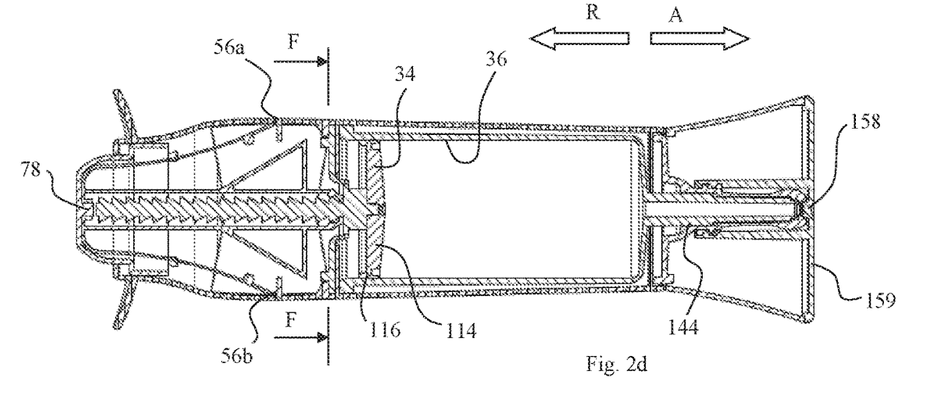
Figures 2E, 2F:
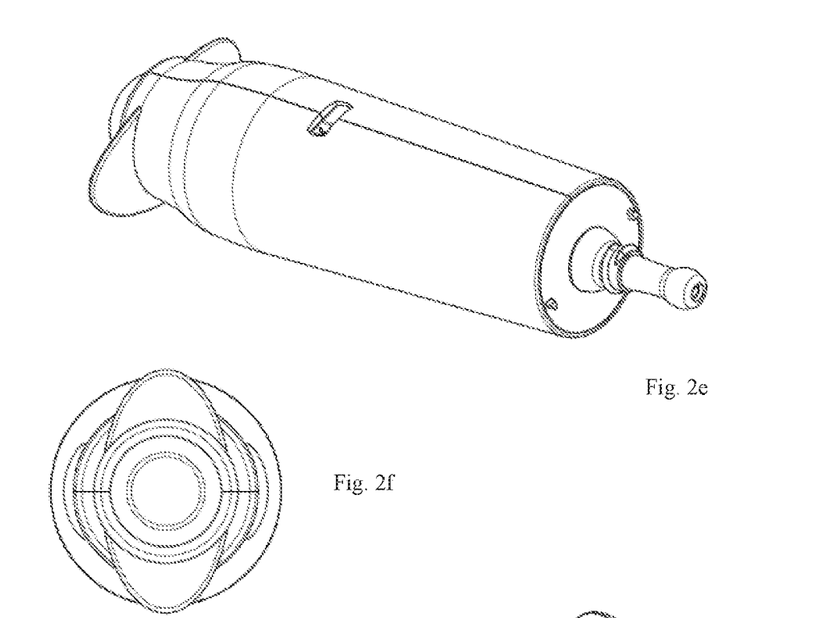
Figures 2G, 2H:
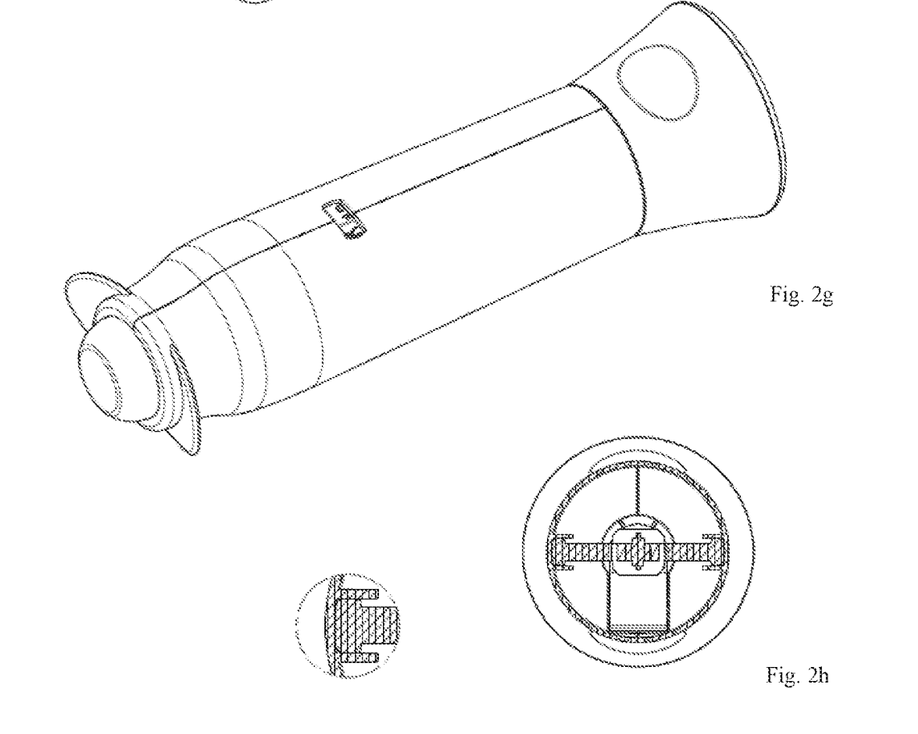

The piston 20 comprises a piston head 34 configured to slide in the barrel 24, along the X-axis, maintaining a sealed contact between the inner surface 36 of the barrel and the piston head 34 (FIG. 2d).

The piston 20 further comprises a piston rod 38, a distal end 40 of which is attached to the piston head 34, and a proximal end 42 of which, opposite the distal end 40, is free.

The button 22 comprises a slider 44 movable in translation along the X-axis and cooperating with a rack, in this case a set of teeth 46 arranged on the piston rod 38, so that the piston rod 38 only follows the movement of the slider 44 when the latter displaces towards the cannula 26 (forward direction A). The button also comprises a push-button 48 coupled with the slider 44 and operable, from the outside of the case 12, by an operator.

Slider

The slider 44 (FIG. 3c) extends in the horizontal median plane. It comprises, at the distal end thereof, a substantially transverse base 50, i.e. extending in a plane perpendicular to the X-axis.

The slider comprises a spring 51, in the form of two spring arms 52a and 52b which, acting as leaf springs, extend from the base 50 towards the distal end of the dispenser in the median horizontal plane. Each spring arm 52a and 52b diverges progressively away from the X-axis to an abutment end 54a and 54b, respectively abutting against the shoulders 56a and 56b defined by the case 12 (FIG. 2d). The abutment ends 54a and 54b on the shoulders 56a and 56b advantageously prevent the rotation of the slider 44 about a vertical axis perpendicular to the horizontal median plane.

The spring arms taper progressively as one approaches the abutment ends, at least over part of the length thereof.

The shape of the spring arms is adapted to allow their deformation, in the horizontal median plane, when a force is exerted by means of the push-button 48 on the base 50, along the X-axis and towards the distal end of the dispenser. As a result of this deformation, the curvature of the spring arms increases. When this force disappears, the elasticity of the spring arms allows them to return to their original shape.

The slider 44 further comprises two pawl arms 58a and 58b extending, substantially along the X-axis, between the spring arms 52a and 52b.

The spring arms and pawl arms extend in substantially the same plane. The pawl arms are spaced apart from each other so that the piston rod 38 may be accommodated between said pawl arms.

More precisely, each pawl arm 58a-58b (FIG. 3c) comprises:

a longitudinal portion 60a-60b which, from the base 50, extends along the X-axis towards the distal end of the dispenser, beyond the abutment ends of the spring arms, and a clamp portion 62a-62b, which extends the longitudinal portion 60a-60b and comes into contact with the piston rod.

The two pawl arms and the base 50 thus have the general shape of a clamp, similar to a tweezer, that elastically clamps the piston rod 38. The clamping action results in the application, by the clamp portions, of two opposite forces, oriented towards the horizontal median plane.

Figures 3D, 3E:
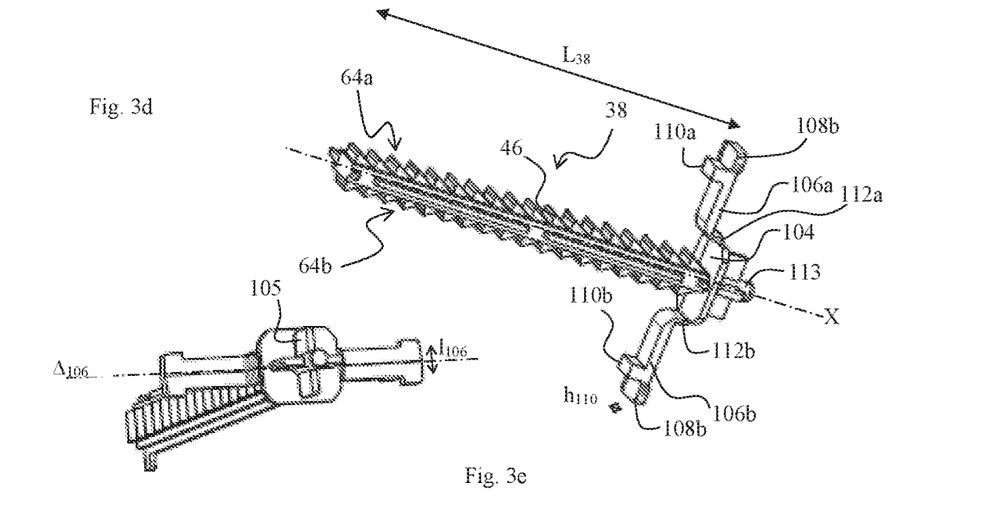
Figure 4A:
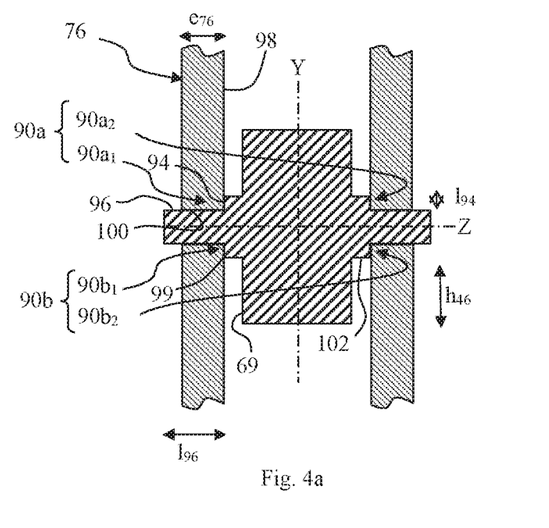

In the clamping region, the piston rod 38 has a rack formed on two opposite sides of the piston rod by rows of teeth 64a and 64b (FIG. 3d). The rows of teeth 64a and 64b cooperate with the clamp portions 62a and 62b, respectively, to ensure an irreversible advancement of the piston. For this purpose, each tooth 46 comprises a substantially transverse and substantially rectangular locking side 66, an inclined side 68 which, from the locking side, approaches the X-axis as one approaches the distal end of the dispenser, and two lateral vertical sides 69 (FIG. 4c). The locking side 66 of a tooth in a row of teeth 64a or 64b is shaped so as to block the advancement of the clamp portion 62a or 62b, respectively, in the forward direction A. Conversely, the inclined side 68 of any tooth in a row of teeth 64a or 64b is shaped to allow sliding contact by the clamp portion 62a or 62b, respectively, towards the proximal end of the dispenser.

Preferably, all the teeth 46 of a row of teeth are identical, preferably, all the teeth of both rows of teeth are identical. Preferably, the height $h_{46}$ of a tooth 46 is greater than 0.1 mm, preferably greater than 0.2 mm, preferably greater than 0.5 mm, even greater than 1 mm, and/or less than 5 mm, preferably less than 3 mm. Preferably, the length $L_{46}$ of a tooth 46 is greater than 1 mm, preferably greater than 2 mmn and/or less than 6 mm, preferably less than 5 mm, respectively.

More preferably, the width $l_{46}$ of a tooth 46 is greater than 1 mm and/or less than 8 mm. Preferably, it is substantially identical to the width $l_{62}$ of the clamp portion with which the tooth 46 cooperates.

The number of teeth is not limited. Preferably, the number of teeth in a row of teeth is greater than 10, greater than 15 and/or less than 30, less than 25, or less than 20.

The slider 44 further comprises stop arms 70a and 70b to limit the forward stroke of the slider along the X-axis. Preferably, the stop arms 70a and 70b are attached to pawl arms 58a and 58b, respectively. More preferably, they extend substantially transversely. In one embodiment, the two ends of each stop arm are connected to a same pawl arm, one of said ends being connected by means of a stiffening arm 72a-72b.

Preferably, the stop arms and stiffening arms extend in the same plane as the pawl arms and, more preferably, in the same plane as the spring arms. More preferably, the widths, measured perpendicular to the general plane of the slider 44, of the base 50 and/or the spring arms 52a-52b and/or the pawl arms 58a-58b and/or the stop arms 70a-70b and/or the stiffening arms 72a-72b are identical.

The dispenser comprises means to guide the forward movements, i.e. in the forward direction A, and reverse movements, in the opposite direction, i.e. the "reverse direction" R, of the slider 44. Preferably, these guidance means are shaped in such a way that only one translation along the X-axis is allowed.

For this purpose, the dispenser has two pairs 74a and 74b of guide ribs 76a$_1$ and 76a$_2$, and 76b$_1$ and 76b$_2$, respectively. Preferably, the pairs of guide ribs 74a and 74b are made in one piece with the case 12 and, preferably with the half-cases 12a and 12b, respectively. The distance $d_{74a}$ or $d_{74b}$ between the guide ribs 76a$_1$ and 76a$_2$ or 76b$_1$ and 76b$_2$, respectively, corresponds substantially to the width of the stop arms and/or the stiffening arms and/or the pawl arms and/or the spring arms, being slightly greater than this width so as to allow a guided sliding of the slider between said guide ribs. Preferably, the thickness of the different parts of the slider 44 that may penetrate between the guide ribs of a pair of guide ribs during the back and forth movement of the slider 44 is constant, thus improving the quality of the guidance.

Preferably, the base 50 abuts against the bottom of the push-button 48. More preferably, the slider 44 is attached on the bottom of the push-button 48, for example by inserting a tenon 78 of the push-button into a corresponding seat on the base 50 of the slider 44.

In a preferred embodiment, the push-button 48 is made of a rigid material. It preferably has a peripheral flange 80 which, in cooperation with an annular flange 82 of the case 12, limits the reverse movement of the push-button 48.

More preferably, the push-button 48 is hollow, which advantageously limits the axial footprint of the dispenser, the pawl arms 58a and 58b and the spring arms 52a and 52b being able to extend substantially to the bottom of the push-button 48.

As described above, the slider 44 allows a forward movement to be transmitted to the piston rod 38 by the cooperation of the clamp portions 62a and 62b with the teeth of the rows of teeth 64a and 64b respectively.

The maximum reverse position of the piston 20 preferably corresponds to the initial configuration of the dispenser before its first use (FIG. 2). In the initial configuration, the rows of teeth 64a and 64b face the pawl arms 58a and 58b, respectively, and preferably the piston head 34 seals the proximal opening 86 of the barrel 24.

More preferably, the length $L_{58}$ of the pawl arms is substantially equal to the length of the piston rod $L_{38}$. In the maximum reverse position of the piston 20, as shown in FIG. 2d, the piston rod 38 may be advantageously accommodated between the two pawl arms 58a and 58b, the proximal end 42 of the piston rod 38 being in the immediate vicinity of the base 50. This improves the compactness of the dispenser.

In a preferred embodiment, the rows of teeth 64a and 64b extend over the entire length of the piston rod. The forward stroke of the piston 20 may thus be advantageously maximized, since it may reach the full length $L_{38}$ of the piston rod.

The forward movement of the piston rod is guided by the guide ribs 76a$_1$, 76a$_2$, 76b$_1$ and 76b$_2$ so that the piston rod may only move along the X-axis, excluding any rotation. For this purpose, as shown in FIG. 4a, first and second pairs 90a and 90b of corners 92a$_1$ and 92a$_2$, and 92b$_1$ and 92b$_2$, respectively, are provided along the piston rod 38. The corners of the first and second pairs 90a and 90b extend along and on each side of the first and second rows of teeth, respectively.

Each corner 92 defines a vertical side 94 and a horizontal side 96 which are in sliding contact with a large side, in this case an inner side 98, and an edge 100, respectively, of a corresponding guide rib 76, as shown in FIG. 4a.

More precisely, the edges of the guide ribs 76a$_1$ and 76a$_2$, respectively, are coplanar and abut against the coplanar horizontal sides of the corners 92a$_1$ and 92a$_2$, respectively.

Similarly, the edges of the guide ribs 76b$_1$ and 76b$_2$, respectively, are coplanar and abut against the coplanar horizontal sides of the corners 92b$_1$ and 92b$_2$ respectively.

The inner sides of the guide ribs 76a$_1$ and 76a$_2$, respectively, abut against the vertical sides of the corners 92b$_1$ and 92b$_2$, respectively. The inner sides of the guide ribs 76b$_1$ and 76b$_2$, respectively, abut against the vertical sides of the corners 92b$_1$ and 92b$_2$, respectively.

The vertical sides of the corners 90a$_1$ and 90b$_1$ are coplanar, as are the vertical sides of the corners 90a$_2$ and 90b$_2$.

To improve the quality of the guidance, each guide rib 76 preferably has an edge 100 that extends parallel to the X-axis. The length of the edge 100 is preferably more than 5 mm, preferably more than 10 mm.

The height $h_{76}$ of a guide rib, measured from the case to the edge 100, is preferably the same, whichever the guide rib considered.

This arrangement effectively limits any rotation of the piston od around the X-axis.

This reduces manufacturing costs. This also improves the compactness of the dispenser.

The presence of the four guide ribs, cooperating with four respective corners of the piston rod 38, ensures precise and reliable guidance of the piston rod 38.

Preferably, the thickness $e_{76}$ of a guide rib is greater than 0.3 mm and/or less than 2 mm. Preferably, the thickness $e_{76}$ is substantially equal to the width $l_{96}$ of the horizontal side 96 of the corner 94 with which the guide rib 76 cooperates. In a preferred embodiment, the width $l_{96}$ of a horizontal side 96 is greater than 0.3 mm and/or less than 2 mm.

In a preferred embodiment, the width $l_{94}$ of the vertical side 94 of a corner is less than 2 mm, preferably less than 1 mm. Preferably, the width $l_{94}$ of the vertical side of a corner 92 is less than the height $h_{46}$ of the teeth of the row of teeth along which said corner extends.

More preferably, the four corners are substantially identical and/or the four guide ribs are substantially identical.

Preferably, in any cross section, as shown in FIG. 4a, the cross-section of the piston rod has two axes of symmetry Y and Z. Preferably, it has the general shape of a cross when it intersects a tooth.

Preferably, the vertical side 94 of a corner does not extend in the plane of a lateral side 69 of a tooth. In a preferred embodiment, a flange 102, preferably substantially horizontal, connects the vertical side 94 of a corner to the lateral side 69 of the teeth of the row of teeth that extends along said corner. The edge 99 delimiting the vertical side 94, on the side opposite the junction line between the vertical side 94 and the horizontal side 96 of a corner, is preferably straight and extends preferably parallel to the X-axis. The reliability of the guidance is thus improved.

The distal end 40 of the piston rod 38 defines a transverse plate 104, which abuts against the piston head 34. Advantageously, this abutment prevents any rotation of the piston head around an axis different from the X-axis. Preferably, the plate 104 is extended by one or more fins 105 which penetrate into the piston head, thus avoiding any rotation of the piston head around the X-axis. The fins 105 preferably extend in longitudinal, preferably radial, planes.

Reciprocally, the plate 104 allows the piston rod 38 to benefit from the guidance of the piston head 34 provided by the barrel 24.

Locking Device

The dispenser comprises a locking device, in the form of two tabs 106a and 106b (FIG. 3e). The tabs extend in a transverse plane.

Preferably, the tabs are inside the case, and are not accessible by the operator. The safety is thus improved.

The tabs are aligned along a transverse tab axis $\Delta_{106}$, which intersects the X-axis.

The tabs 106a and 106b are attached to the plate 104 by radially inner ends 112a and 112b, respectively. The junction zone between an inner end 112 and the plate 104 is a weakened zone, which is breakable when the piston rod 38 is pressed in the forward direction, in particular, when the operator presses the push-button, for example with his thumb.

The weakened zone is in the form of a weakened line, preferably perpendicular to the X-axis, for example extending substantially vertically. The weakened line may result from a local reduction of thickness or the presence of through holes.

Each tab 106a and 106b comprises a radially outer end 108a and 108b, respectively, attached to the case 12, preferably to the half-cases 12a and 12b, respectively. Preferably, each radially outer end 108a and 108b is attached by insertion into a corresponding seat arranged on the case, in particular between the rib pairs $76a_1$-$76a_2$ and $76b_1$-$76b_2$, respectively. Preferably, the attachment is obtained by snap-fitting.

In a preferred embodiment, the tabs 106a and 106b extend at least partially between the guide ribs of the pairs 74a and 74b, respectively. Preferably, the width $l_{106}$ of the tabs 106a and 106b (outside their end parts; see FIG. 3e), is substantially equal to the distance between the two guide ribs between which they extend. Advantageously, the guide ribs thus contribute to keeping the tabs in position, which is particularly useful after breaking the junction zone.

Preferably, the tabs 106a and 106b are used as stops for the stop arms 70a and 70b, respectively, to limit the advancement of the slider 44.

For this purpose, preferably the tabs 106a and 106b each have, preferably near the radially outer ends thereof, a stop pin 110a and 110b, respectively.

Each time the push-button is pressed to administer a dose, the slider 44 advances from its rest position wherein the peripheral edge 80 of the push-button abuts against the case to the maximum advanced position wherein the stop arms 70 abut against the stop pins. The slider drives the piston. The height $h_{110}$ of the stop pins thus determines the dosing stroke, i.e. the advancement of the piston 20 each time the push-button is pressed.

Preferably, the height $h_{110}$ is determined so that the dosing stroke is equal to the length $L_{46}$ of a tooth. Each time the push-button is pressed, the piston advances thus along the X-axis by a distance $L_{46}$.

Preferably, the piston rod 38 (which comprises the plate 104) and the tabs 106 constitute a one-piece part, for example, manufactured by injecting plastic into a mold.

Advantageously, the height of the stop pins 110 may then determine a dosing stroke necessarily equal to the length of one or several teeth $L_{46}$, which optimizes the dosing precision.

This feature is particularly advantageous for changing the volume of each dose administered by the dispenser. It is enough to change the one-piece part by replacing it with another similar part, to have, for example, a longer tooth length and lower stop pins for an increased dosing stroke.

Since the stop pins are initially attached to the piston having the rack, the operator is not likely to use a rack and stop pins that do not match. The assembly of the dispenser is thus easier and more certain.

Piston

The distal end 40 of the piston rod 34 has an attaching tenon 113 with an X-axis inserted and attached in a corresponding seat of the piston head 34, substantially in the center of the piston head.

The piston head 34, on the X-axis, has a seal holder 114 generally disc-shaped, and a seal 116 preferably housed in a circumferential groove of the seal holder 114 so as to ensure a seal between the inner surface 36 of the barrel and the piston head 34 (FIG. 2d).

In a preferred embodiment, the seal holder 114 comprises stiffening ribs 118, preferably substantially radial, which advantageously limits the weight of the seal holder and the amount of material used to make it.

The front side 120 of the seal holder 114 is preferably of a shape complementary to the bottom 122 of the barrel 24 wherein the cannula lumen 28 opens. Preferably, the length of the piston rod 38 is enough for the front side of the seal holder 114 to reach the bottom 122 of the barrel 24. The length of the forward stroke of the piston head in the barrel 24 is preferably substantially identical to the length of the piston rod 38. Advantageously, the barrel 24 may thus be completely emptied, which limits product losses.

Preferably, the length of the piston rod is determined so that, in this extreme position of the piston 20, corresponding to a "final configuration", the clamp portions 62 of the slider 44 are upstream of the locking sides 66 of the "last" teeth 46, i.e. those located at the proximal end 42 of the piston rod 38. The compactness of the dispenser is thus optimal.

Barrel

The barrel 24, on the X-axis, has a constant cross-section along the X-axis, preferably circular. Its proximal opening 86 is bordered by a flange 123, which extends in a substantially transverse plane and is generally annular in shape. The flange 123, however, has a straight portion, in the form of a flat spot 124, which is substantially horizontal. Three longitudinal support ribs 134 are made in one piece with the barrel. Their straight edge 135 extends from the outer surface 132 of the barrel to the flat spot 124.

Indicator Label

An indicator label 126 is attached by a proximal end 128 on the piston 20. For example, in the embodiment shown, the proximal end 128 comprises an orifice through which the attaching tenon 113 passes, so that said proximal end 128 is sandwiched between the plate 104 and the seal holder 114. The distal end 130 of the indicator label is free. The indicator label 126 extends, substantially along the X-axis, preferably substantially flat, between the case 12 and the outer surface 132 of the barrel 24, resting on the flat spot 124 and on the support ribs 134.

On its outer side, the indicator label has indicators 137, for example numbers and/or colors, preferably an ordered sequence of numbers that increase or decrease as one approaches the distal end 130 of the indicator label 126. A window 138, located in the case 12, is configured so that the operator may see at least one indicator 137, preferably only one indicator 137 through the window 138.

The pitch, i.e. the distance along the X-axis between two successive indicators 137, is substantially equal to the dosing stroke. Advantageously, the indicator 137 visible through the window 138 thus changes each time a dose is administered. Looking through the window 138 thus makes it possible, for example, to read a number corresponding to the number of doses already administered or the number of doses that may still be administered.

Attaching the proximal end 128 of the indicator label to the piston allows this end to be pulled toward the inside of the barrel as the piston advances in said barrel. The indicator label is flexible enough to bend 180° to bypass the flange 123 of the barrel in a reversible way. It may notably be made of paper and/or plastic.

The support ribs 134 facilitate the displacement of the indicator label 126 and its rotation around the flat spot 124. The flat spot 124 also allows, advantageously, to give a flat shape to the indicator label in the area of the window 138.

Applicator Tip

The applicator tip 16 is intended to facilitate the application of the product on the skin of an animal.

Figure 3F:
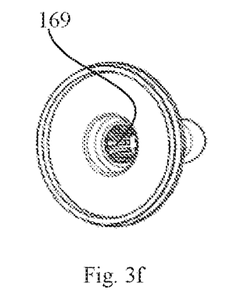
Figure 3G:
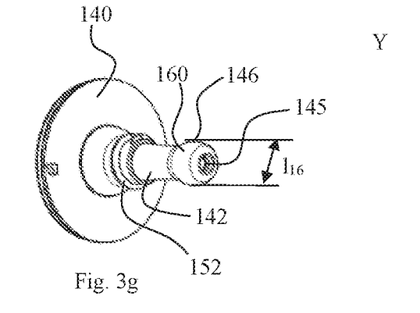
Figure 3H:
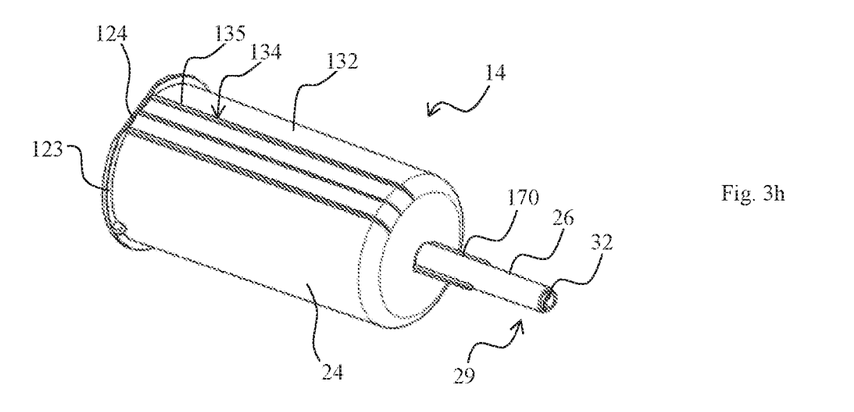

Preferably, the applicator tip (FIGS. 3f and 3g) is thus atraumatic, and in particular does not have a pointed shape. Preferably, the distal end of the applicator tip has a width $l_{16}$, measured in a transverse plane, greater than 1 mm, greater than 2 mm, or greater than 3 mm. The distal end 146 of the applicator tip preferably has a protuberance 160 with no sharp angles, preferably substantially spherical, which limits the risk of injury while administering the product. The curvature radius of the protuberance is preferably greater than 1 mm, 2 mm or 3 mm.

The applicator tip 16 shown has an annular base 140 extended axially, on the proximal side, by a nipple 142.

The applicator tip may be attached to the case 12 by any means, for example by clipping the annular base 140 onto the case. In one embodiment, the applicator tip 16 is detachably mounted on the case. Advantageously, it may thus be replaced by a tip which is better adapted to the product to be applied or to the animal to which the product is to be applied.

A tip lumen 144 passes, along the X-axis, through the length of the annular base and the nipple 142 and opens axially outwards through an ejection orifice 145 at the distal end 146 of the nipple 142. The cannula 26 is housed in the tip lumen 144 until it reaches substantially the distal end 146 of the nipple.

Figure 4B:
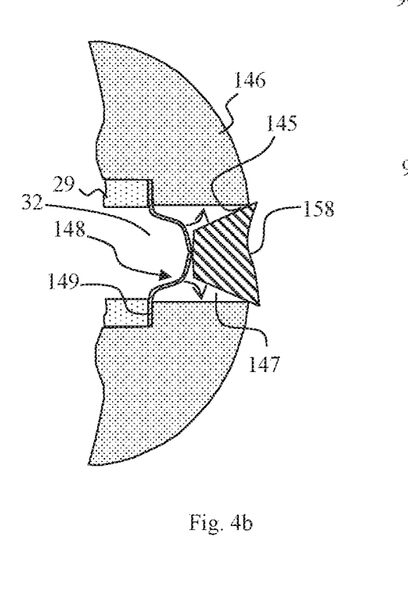
Figure 4C:
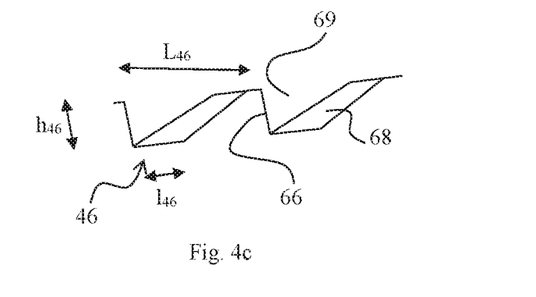

A check valve 148 (FIG. 4b) is however sandwiched between the distal end 29 of the cannula 26 and the distal end 146 of the nipple (FIG. 4b). The outlet orifice 32 of the cannula is thus axially slightly displaced upstream relative to the ejection orifice 145. The duct 147 extending between the outlet orifice 32 and the ejection orifice 145 is preferably less than 1 mm long.

The check valve seals the outlet orifice 32 of the cannula. It is configured to open under the effect of an overpressure in the barrel (arrows in FIG. 4b), which allows the product initially contained in the barrel to be ejected, and to remain closed in the absence of such an overpressure, which guarantees optimal conditions of hygiene.

The check valve, for example made of a polymeric material, for example rubber, may in particular be a flexible slit membrane, with a dome shape. As shown in FIG. 4b, the check valve has a flange 149 sandwiched and compressed between the nipple 142 and the cannula 26. Advantageously, the edge 149, preferably annular, ensures a seal between the nipple and the cannula, preventing any leakage of product between the cannula and the nipple.

To ensure a predetermined angular positioning, around the X-axis, the applicator tip 16 and the barrel on the case 12, the inner surface of the nipple, defining the lumen 144, comprises one or more longitudinal grooves 169 (FIG. 3f) wherein are housed one or more error-proofing ribs 170, arranged on the outer surface of the cannula of the barrel.

The same error-proofing ribs 170 are also housed in notches 172 having a corresponding shape in the case.

Cap

Figure 3I:
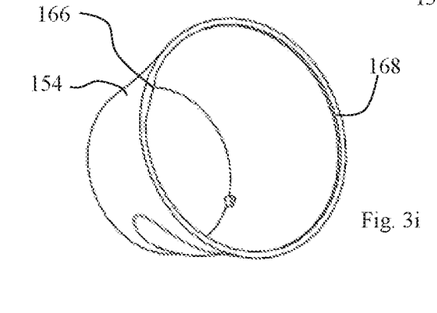
Figure 3J:
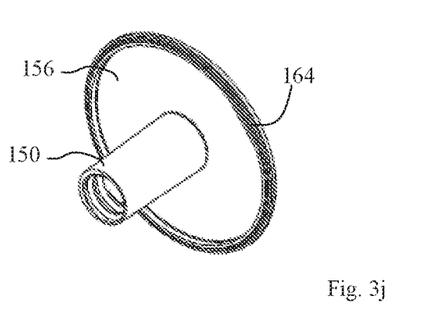

The cap 18 (FIGS. 3i and 3j) preferably has an inner skirt 150, internally threaded so as to be screwed onto a nipple thread 152, and an outer skirt 154, the inner and outer skirts being connected to each other by a transverse camber 156, in the form of a disc.

Preferably, the cap 18 consists of two parts attached to each other, namely the outer skirt 154 on one side and a part consisting of the inner skirt 150 and of the transverse camber 156, these parts being preferably welded to each other at the periphery of the camber 156.

The length of the inner skirt 150 is determined so that, in the closed position of the cap, corresponding to a maximum screwing of the cap onto the nipple thread 152, the transverse camber 156 seals the ejection orifice 145 of the nipple. Preferably, the transverse camber comprises a stud 158 configured to seal the check valve 48 in the closed position of the cap. Preferably, the stud 158 penetrates into the duct 147 (FIG. 4b), preferably so as to close in a sealed manner the ejection opening 145, more preferably by abutting against the check valve to prevent it from opening. This improves conditions of hygiene, as no drops of the product may escape from the dispenser with the cap 18 in the closed position.

The sealed closure of the ejection orifice 145 by the cap in the closed position also advantageously prevents the piston 20 from moving in the reverse direction R.

The front surface of the cap 159 is preferably flat. It preferably has a surface area greater than 3 cm², 5 cm², 8 cm², allowing the dispenser to be stood upside down. Preferably, the dimensions of the front surface 159 are adapted so that the vertical axis passes through the barycenter of the dispenser through said front surface when the dispenser is stood upside down on a plane inclined by 5°, preferably 10°, preferably 15°, preferably 20°, with respect to a horizontal plane. Stood upside down, i.e. with said front surface 159 in contact with said inclined plane, the valve is thus stable. It is thus advantageously easy to store.

The outer skirt 154 preferably has locking means to lock the cap 18 onto the case 12 or onto the applicator tip 16. Preferably, these locking means are activated by simply screwing the cap onto the nipple thread 152. Preferably, these locking means may not be unlocked solely by unscrewing the cap. Preferably, they require deformation of the outer skirt 154, preferably by pressing on the unlocking regions 162, preferably arranged in relief on the outer skirt 154. The locking means may, for example, consist of well-known clipping means.

Screwing the cap onto the nipple thread 152 brings the outer skirt 154 into an angular position around the predefined X-axis, arranged so that the locking means may be activated at the end of screwing and deactivated by pressing on the unlocking regions 162 in the screwed-on position.

To ensure an adequate angular positioning of the unlocking regions 162 in the screwed-on position of the cap, the transverse camber 156 preferably has an error-proofing device 164, in particular in the form of a flat surface that is precisely positioned along a corresponding straight edge 166 of the distal flange 168 of the outer skirt 154.

The unlocking means are an advantageous way of limiting the use of the dispenser by children.

Assembly

The assembly of a dispenser according to the invention is particularly simple.

The operator mounts the piston head on the piston rod, sandwiching the proximal end 128 of the indicator label 126. The tabs 106 are still attached to the piston rod.

He inserts the tenon of the push-button 78 into the corresponding slot of the slider 44.

The operator then moves the clamp portions 62a and 62b apart, then inserts the proximal end of the piston rod 38 between these clamp portions, until the clamp portions may elastically abut against the first teeth of the two rows of teeth and the plate 104. He then releases the clamp portions for this purpose.

After inserting the piston head into the opening of the barrel 24, he inserts the assembly formed of the push-button, the slider, the piston and the barrel between the two half-cases 12a and 12b.

The radially outer ends 108a and 108b of the tabs 106a and 106b, respectively, are inserted, preferably snap-fitted, into the corresponding seats arranged in the half-cases 12a and 12b, respectively.

The presence of the tamper-proof tabs 106a and 106b speeds up assembly considerably, facilitating and guaranteeing the correct positioning of the stop pins, but also of the piston rod between the ribs.

The operator then attaches the half-cases 12a and 12b to each other.

He then attaches the applicator tip 16 to the case 12 by inserting the cannula into the tip lumen 144 and sandwiching the check valve 148 between the distal end 150 of the cannula and the distal end 146 of the nipple 142.

The error-proofing ribs 170 on the outer surface of the cannula of the barrel, the longitudinal grooves 169 inside the nipple and the notches 172 on the case ensure the correct angular positioning of the applicator tip 16 and the barrel in relation to the case 12.

In addition, to manufacture the cap, the outer skirt 154 is welded to the transverse camber 156, the angular position around the X-axis being predetermined by the cooperation of the error-proofing device 164 of the transverse camber 156 and the straight edge 166 of the distal flange 168 of the outer skirt 154. It is sufficient to screw on the cap to close the ejection orifice and activate the safety lock.

The barrel may be filled with the product to be dosed using any known means, for example before introducing the piston head into the barrel.

In a preferred embodiment, the tabs 106a and 106b are only used to facilitate assembly, as described above. They are thus preferably deactivated before the dispenser is sold.

Preferably, the dispenser is manufactured according to steps a) to c) described above.

In step a), the different components of the dispenser are assembled, preferably as described above. The barrel is filled, at least partially, with a liquid product, preferably a veterinary product. The techniques for this purpose are known. In particular, the barrel may be filled through the proximal opening 86 thereof, before the piston is inserted, or through the cannula 26, before or after the piston is inserted.

In step b), the push-button 48 is pressed along the X axis, preferably once. This pressure causes the breakage of the junction areas of the tabs 106a and 106b with the plate 104, and then the displacement of the button 22 and the piston 20 in the forward direction. The advancement of the piston 20 pushes product into the cannula 26.

Preferably, the cannula lumen 28 is not completely filled with product in step a), and the filling of the barrel in step a) is performed in such a way that the advancement of the piston in step b) fills, at least partially, preferably completely, the empty volume of this lumen.

The complete filling of the cannula lumen 28 allows the dispenser to be operational, i.e. to administer a dose of product, as soon as the push-button is pressed again. Priming also ensures that the first dose administered will have the same volume as the following ones, which is particularly beneficial for products with a therapeutic or prophylactic effect.

More preferably, the remaining empty volume in the cannula lumen 28 at the end of step a) is equal to the volume of product pushed into said cannula in step b). Advantageously, no product is thus wasted in step b).

In step c), the dispenser is packaged in packaging suitable for its sale. It may be placed in individual packaging, for example a box, preferably covered with a packaging film, or a blister pack. It may be placed in a collective packaging, for example placed in a box with other dispensers.

The packaging is preferably hermetic so that the user may be sure that the dispenser purchased is new.

Use

The use of the dispenser is directly deduced from the preceding description. The valve is initially in the position shown in FIG. 2.

The operator presses on the locking regions 162 in order to compress the outer skirt 154 and unlock the locking means. He may then unscrew the cap. Unscrewing the cap releases the stud 158 from the ejection orifice.

The operator then applies the protuberance 160 of the nipple 142 onto the animal's skin. The rounded shape of this protuberance limits the risk of injury. In the same way as in operating a syringe, he then presses the push-button 48, holding the dispenser with his index and middle finger arranged behind the lugs 13a and 13b on the distal side, in the manner of a syringe.

The displacement of the push-button 48 along the X-axis is convenient because it allows the product to be administered with only one hand. This feature is particularly advantageous when the product is to be applied on the skin of a nervous animal.

If the deactivation has not already been carried out at the factory, the tabs 106 are still attached to the plate 104 when the dispenser is first used. The advancement of the push-button is thus hindered by the junction zones between the plate 104 and the tabs 106. The operator must thus press the push-button 48 relatively forcefully in order to break these junction zones. The push-button thus constitutes a device for deactivating the tabs.

After the first press of the push-button 48, the tabs are thus broken from the plate 104 and irreversibly deactivated. They no longer hinder the displacement of the piston head in the barrel as a result of successive presses of the push-button 48.

The breakage of the junction zones of the tabs may advantageously be carried out in the same movement as the first administration of a dose. The use of the dispenser is thus more efficient and more convenient.

After deactivating the tabs, the push-button 48 may advance in the forward direction A, driving with it the base 50 of the slider 44. The abutment of the spring arms 52 on the shoulders 56 opposes this advancement. However, the spring arms 52 have a flexibility that allows them to bend elastically towards the X-axis, thus allowing the base 50 to advance.

The clamp portions are also in contact with the plate 104. The advancement of the base 50 therefore leads to the advancement of the piston head into the barrel. The overpressure resulting from this advancement leads to the opening of the check valve 148. The product may therefore be ejected from the dispenser through the ejection orifice.

The piston head continues to advance until the stop arms 70a and 70b come into contact with the stop pins 110a and 110b, respectively.

The operator then releases the pressure on the push-button 48. Due to the elasticity of the spring arms 52a and 52b, the slider 44, and thus the push-button 48, move back in the reverse direction R to their initial position, i.e. until the peripheral edge 80 of the push-button 48 comes into contact with the annular edge 82 of the case.

During this reverse movement, the clamp portions 62a and 62b slide on the inclined sides 68a and 68b of the most distal teeth of the two rows of teeth, said "first teeth". The elasticity of the pawl arms 58a and 58b allows the clamp portions 62a and 62b to spread apart from the X-axis, sliding on the inclined sides 68a and 68b of the first teeth. This sliding does not allow the recoil action produced by the spring arms 52a and 52b to be opposed. This sliding also does not allow the piston to move backwards, which is held in position by the friction of the seal 116 on the inner surface of the barrel, but also, advantageously, by the closing of the check valve 148, which prevents the entry of air into the barrel, and thus the retreat of the piston, the product inside the barrel being substantially incompressible.

Substantially at the moment when the peripheral flange 80 of the push-button abuts against the annular flange 82 of the case 12, or slightly before, the clamp portions 62a and 62b exceed the proximal limit of the inclined sides 68a and 68b of the first teeth on which they slide, and, under the effect of the elasticity of the pawl arms, return towards the X-axis, positioning themselves in front of the locking sides 66a and 66b of the first teeth.

As the push-button moves back and forth, the guide ribs 76 advantageously ensure efficient guidance of the slider 44, but also of the piston rod 38.

The dispenser is thus in a suitable position for administering a second dose.

If the operator does not need to administer a second dose immediately, he screws the cap 18 back onto the nipple thread. At the end of screwing, the locking means are automatically activated, which prevents children from opening it.

In addition, the stud 158 located at the bottom of the cap penetrates into the nozzle lumen 144, compressing, in a sealed manner, the check valve and/or closing, in a sealed manner, the ejection orifice. This means that no product may escape into the cap, for example due to agitation of the dispenser, thus ensuring cleanliness.

Moreover, the penetration of the stud prevents the product from emerging from the ejection orifice during the next use, thus preventing any unintentional contact of the product with the operator's skin.

The second dose is administered in the same way as the administration of the first dose. However, the advancement occurs by pressure on the pawl arms on the locking side of the first teeth, and no longer on the plate 104.

Each time a dose is administered, the piston advances a distance equal to the length of a tooth, in the example shown.

The following doses are administered as in the administration of the second dose, by pushing the pawl arms on the locking sides of the successive teeth.

The back-and-forth movements of the push-button along the X-axis thus allow the administration of a plurality of doses, all identical, in a simple and fast way.

During the last dosing stroke, the piston head is positioned against the bottom of the barrel 122, thus ensuring a complete emptying of the barrel. The clamp portions 62 are then in contact with the locking sides of the most proximal teeth, or "last teeth" of the two rows of teeth.

The device may then be discarded.

Initially, the operator may see a number, for example "18", through the window 138, indicating the number of doses remaining to be administered. Advancing the piston head into the barrel drives the indicator label 126 towards the inside of the barrel and changes the region of the indicator label visible through the window 138. The visible number preferably decreases by one unit with each administration of a dose. This allows the operator to easily evaluate the barrel filling level, but also to snake sure that the treatment is correctly followed.

In one embodiment, at the first dosing stroke, during which the tabs are separated from the plate 104, the liquid expelled from the barrel fills the cannula lumen 28, initially at least partially empty. No product is thus ejected from the dispenser.

Advantageously, the operator may thus dissociate the operation by which he detaches the tabs and the following operations by which he administers the product.

In this embodiment, the first two indicators 137 on the indicator label may be identical, for example equal to "18". Preferably, the first indicator 137 is however used to indicate that the tabs have not yet been deactivated. For example, a letter "A" may appear in the window before they are deactivated.

As is now clearly apparent, the invention provides a compact, easy-to-use dispenser, consisting of a very small number of parts, easy to assemble, ergonomic and practical to use, allowing the number of doses already administered, or remaining to be administered, to be assessed, reliable, ensuring optimal health and safety conditions and at a reduced cost.

Naturally, the invention is not limited to the embodiments described and represented, which are provided for illustrative purposes only.

In particular, the tabs could be attached on another part of the piston than the plate 104, for example on the seal holder 114.

The reverse movement of the slider may lead to a sliding of the abutment parts successively over several successive teeth. Preferably, however, the dosing stroke corresponds to a sliding on a single tooth.

The teeth could be replaced by holes, whether through or not, provided that the shape of the abutment parts is adapted accordingly, for example to take the form of hooks or claws hooking the edge of said holes in the forward direction and leaving said holes in the reverse direction.

The barrel could be removable.

The case is optional in that it could, for example, be replaced by a barrel with a suitable shape.

The spring could take another form, and in particular be helical, compressed air, with contiguous turns, accordion, elastic, etc.

The invention claimed is:

1. Multi-dose dispenser comprising:
    a product reservoir, on a longitudinal axis, opening at a distal end through an outlet orifice and comprising a barrel;
    a piston comprising
        a piston rod having a rack, and
        at a distal end of the piston rod, a piston head slidably mounted in the barrel along the longitudinal axis;
    a pawl mounted so as to be movable along the longitudinal axis relative to the reservoir and configured to cooperate with the rack so as to drive the piston, along the longitudinal axis, only in a forward direction of the piston in the barrel;
    a spring arranged to push the pawl back along the longitudinal axis in a direction opposite to the forward direction, the spring and the pawl forming a one-piece assembly;
    a case containing the pawl and at least a part of the piston; and
    a push-button projecting out of the case and mounted so as to be movable along the longitudinal axis relative to the case, the push-button being mechanically coupled with the pawl so that pressing the push-button in the forward direction advances the pawl in the forward direction,
    wherein the spring extends in a plane including the longitudinal axis and comprises at least one spring arm diverging from the longitudinal axis, in the forward direction, and
    wherein the at least one spring arm is arranged between two guide ribs configured to guide the deformation of the at least one spring arm in a plane passing through the longitudinal axis.

2. Dispenser according to claim 1, comprising a check valve arranged to seal the outlet orifice and to allow only an outlet of product from the reservoir.

3. Dispenser according to claim 2, wherein the check valve has a flange sandwiched between the reservoir and an applicator tip rigidly integral with the reservoir, so that the flange establishes a seal between the reservoir and the applicator tip.

4. Dispenser according to claim 3, wherein the applicator tip is atraumatic, and wherein a distal end of the applicator tip has a protuberance having a substantially spherical shape, the curvature radius of the protuberance being greater than 1 mm.

5. Dispenser according to claim 3, having a duct extending from the check valve to an ejection orifice through which product initially contained in the reservoir may be ejected from the dispenser, the dispenser comprising a cap adapted to selectively seal, in a closed position, the ejection orifice from the dispenser, the cap comprising a stud arranged to penetrate the duct in the closed position of the cap, so as to close the duct in a sealed manner.

6. Dispenser according to claim 2, having a duct extending from the check valve to an ejection orifice through which product initially contained in the reservoir may be ejected from the dispenser, the dispenser comprising a cap adapted to selectively seal, in a closed position, the ejection orifice from the dispenser, the cap comprising a stud arranged to penetrate the duct in the closed position of the cap, so as to close the duct in a sealed manner.

7. Dispenser according to claim 1, wherein the rack comprises first and second rows of teeth, the rows of teeth extending along the longitudinal axis, and the pawl comprising first and second pawl arms ending in first and second clamp portions, respectively, arranged to elastically clamp the rack by pressing on the first and second rows of teeth, respectively.

8. Dispenser according to claim 7, wherein each pawl arm is arranged between the two guide ribs configured to guide the displacement of the pawl arm in a plane passing through the longitudinal axis, the spacing of the two guide ribs of each pair of guide ribs being substantially equal to the width of a respective pawl arm, so as to guide the deformation and/or displacement of the pawl arm.

9. Dispenser according to claim 1, comprising a deactivatable locking device, configured to prevent the administration of a product contained in the reservoir, and arranged inside the case.

10. Dispenser according to claim 9, wherein the locking device is irreversibly deactivatable.

11. Dispenser according to claim 10, wherein the locking device is irreversibly deactivatable by being breakable.

12. Dispenser according to claim 9, wherein the piston rod and the locking device constitute a one-piece part.

13. Dispenser according to claim 9, wherein the locking device has a stop pin configured to limit the displacement of the pawl along the longitudinal axis, in the forward direction, after deactivation.

14. Method for manufacturing a dispenser packaged in a package, the method comprising the following successive steps:
    a) assembling the different components of the dispenser according to claim 10, and filling the barrel with a liquid product;
    b) deactivating the locking device;
    c) packaging the dispenser in the package.

15. Dispenser manufactured by a method according to claim 14, the barrel containing a veterinary product.

16. Dispenser according to claim 1, comprising an indicator label attached, by a proximal end, on the piston and having a free distal end arranged against an outer surface of the barrel.

17. Dispenser according to claim 16, wherein the case provides a window through which a portion of the indicator label is visible from the outside of the case.

18. Dispenser according to claim 16, wherein the indicator label has indicators, the pitch between two successive indicators along the longitudinal axis being constant and equal to the maximum distance that the pawl may travel along the longitudinal axis in the forward direction.

19. Dispenser according to claim 1, wherein the barrel contains a veterinary product, a veterinary liquid or a veterinary paste.

20. Multi-dose dispenser comprising:
   a product reservoir, on a longitudinal axis, opening at a distal end through an outlet orifice and comprising a barrel;
   a piston comprising
      a piston rod having a rack, and
      at a distal end of the piston rod, a piston head slidably mounted in the barrel along the longitudinal axis;
   a pawl mounted so as to be movable along the longitudinal axis relative to the reservoir and configured to cooperate with the rack so as to drive the piston, along the longitudinal axis, only in a forward direction of the piston in the barrel;
   a spring arranged to push the pawl back along the longitudinal axis in a direction opposite to the forward direction, the spring and the pawl forming a one-piece assembly;
   a case containing the pawl and at least a part of the piston; and
   a push-button projecting out of the case and mounted so as to be movable along the longitudinal axis relative to the case, the push-button being mechanically coupled with the pawl so that pressing the push-button in the forward direction advances the pawl in the forward direction,
   wherein the rack comprises first and second rows of teeth, the rows of teeth extending along the longitudinal axis, and the pawl comprising first and second pawl arms ending in first and second clamp portions, respectively, arranged to elastically clamp the rack by pressing on the first and second rows of teeth, respectively.

21. Dispenser according to claim 20, wherein each pawl arm is arranged between two guide ribs configured to guide the displacement of the pawl arm in a plane passing through the longitudinal axis, the spacing of the two guide ribs of each pair of guide ribs being substantially equal to the width of a respective pawl arm, so as to guide the deformation and/or displacement of the pawl arm.

22. Multi-dose dispenser comprising:
   a product reservoir, on a longitudinal axis, opening at a distal end through an outlet orifice and comprising a barrel;
   a piston comprising
      a piston rod having a rack, and
      at a distal end of the piston rod, a piston head slidably mounted in the barrel along the longitudinal axis;
   a pawl mounted so as to be movable along the longitudinal axis relative to the reservoir and configured to cooperate with the rack so as to drive the piston, along the longitudinal axis, only in a forward direction of the piston in the barrel;
   a spring arranged to push the pawl back along the longitudinal axis in a direction opposite to the forward direction, the spring and the pawl forming a one-piece assembly;
   a case containing the pawl and at least a part of the piston;
   a push-button projecting out of the case and mounted so as to be movable along the longitudinal axis relative to the case, the push-button being mechanically coupled with the pawl so that pressing the push-button in the forward direction advances the pawl in the forward direction, and
   a deactivatable locking device, configured to prevent the administration of a product contained in the reservoir, and arranged inside the case,
   wherein the locking device has a stop pin configured to limit the displacement of the pawl along the longitudinal axis, in the forward direction, after deactivation.

23. Multi-dose dispenser comprising:
   a product reservoir, on a longitudinal axis, opening at a distal end through an outlet orifice and comprising a barrel;
   a piston comprising
      a piston rod having a rack, and
      at a distal end of the piston rod, a piston head slidably mounted in the barrel along the longitudinal axis;
   a pawl mounted so as to be movable along the longitudinal axis relative to the reservoir and configured to cooperate with the rack so as to drive the piston, along the longitudinal axis, only in a forward direction of the piston in the barrel;
   a spring arranged to push the pawl back along the longitudinal axis in a direction opposite to the forward direction, the spring and the pawl forming a one-piece assembly;
   a case containing the pawl and at least a part of the piston;
   a push-button projecting out of the case and mounted so as to be movable along the longitudinal axis relative to the case, the push-button being mechanically coupled with the pawl so that pressing the push-button in the forward direction advances the pawl in the forward direction; and
   an indicator label attached, by a proximal end, on the piston and having a free distal end arranged against an outer surface of the barrel.

24. Dispenser according to claim 23, wherein the case provides a window through which a portion of the indicator label is visible from the outside of the case.

25. Dispenser according to claim 23, wherein the indicator label has indicators, the pitch between two successive indicators along the longitudinal axis being constant and equal to the maximum distance that the pawl may travel along the longitudinal axis in the forward direction.

* * * * *